US008137330B2

(12) United States Patent
Fields

(10) Patent No.: US 8,137,330 B2
(45) Date of Patent: Mar. 20, 2012

(54) EXPANDABLE AND PORTABLE EMESIS RECEPTACLE

(76) Inventor: Janet C. Fields, Pelham Manor, NY (US)

( * ) Notice: Subject to any disclaimer, the term of this patent is extended or adjusted under 35 U.S.C. 154(b) by 1442 days.

(21) Appl. No.: 11/124,337

(22) Filed: May 6, 2005

(65) Prior Publication Data

US 2005/0261644 A1 Nov. 24, 2005

Related U.S. Application Data

(60) Provisional application No. 60/568,711, filed on May 6, 2004.

(51) Int. Cl.
*A61M 1/00* (2006.01)

(52) U.S. Cl. ........... 604/319; 220/9.1; 220/9.2; 220/9.3; 220/9.4; 220/218; 220/548; 206/170; 206/171; 206/173; 206/175; 206/202

(58) Field of Classification Search .................. 604/319; 206/170–191, 202, 218, 548; 220/9.1, 9.2, 220/9.3, 9.4

See application file for complete search history.

(56) References Cited

U.S. PATENT DOCUMENTS

| | | | | | |
|---|---|---|---|---|---|
| 1,583,083 | A | * | 5/1926 | Macaraig | 220/9.2 |
| 2,943,660 | A | * | 7/1960 | Seeger | 383/13 |
| 3,475,767 | A | * | 11/1969 | Friesen et al. | 4/452 |
| 5,116,139 | A | * | 5/1992 | Young et al. | 383/49 |
| 5,964,533 | A | * | 10/1999 | Ziglar | 383/36 |
| 6,520,365 | B2 | * | 2/2003 | Schneider | 220/9.2 |
| 6,892,897 | B2 | * | 5/2005 | Stewart | 220/252 |
| 6,948,632 | B2 | * | 9/2005 | Kellogg et al. | 220/9.4 |
| 6,997,338 | B2 | * | 2/2006 | Sabounjian | 220/9.4 |
| 7,073,942 | B2 | * | 7/2006 | Vazquez | 383/2 |

* cited by examiner

*Primary Examiner* — Tatyana Zalukaeva
*Assistant Examiner* — Ginger T Chapman
(74) *Attorney, Agent, or Firm* — Dickstein Shapiro LLP

(57) ABSTRACT

A liquid receptacle made of a wire frame and a disposable and biodegradable material that is substantially impervious to water. The liquid receptacle is capable of being expanded and collapsed for ease of transportation and storage. For ease of use, the liquid receptacle is shaped with a flat bottom allowing it to stand without support, and equipped with a flap surrounding a top opening of the receptacle. For ease of transportation after use, a cord is supplied around the flap for closing the top opening of the liquid receptacle.

15 Claims, 3 Drawing Sheets

EXPANDABLE AND PORTABLE EMESIS RECEPTACLE

CROSS-REFERENCE TO RELATED APPLICATIONS

The present invention claims the benefit of U.S. Provisional Patent Application Ser. No. 60/568,711, filed May 6, 2004, entitled "Expandable and Portable Emesis Receptacle," the contents of which are hereby incorporated by reference as if set forth fully herein.

BACKGROUND OF THE INVENTION

Millions of children and even adults suffer from motion sickness. Motion sickness bags or "air sickness bags" as they exist today require the user to hold the bag in place over the mouth during an episode of sickness. This requires a certain level of dexterity that children and even some adults do not possess. In addition, these inferior bags are generally only available on airlines and cruise ships.

The average family that travels by car with motion sickness prone children travels with buckets and plastic bags. Motion sickness is also problematic on school field trips and in amusement parks. Therefore, there is a demand for a disposable motion sickness bag that can be stored in a car or glove compartment, can be easily opened, and requires minimal dexterity to use such that even a three year old could use it successfully.

OBJECTS OF THE INVENTION

It is an object of the invention to provide a disposable motion sickness bag.

It is further an object of the invention to provide a motion sickness bag that is packaged compactly.

It is further an object of the invention to provide a motion sickness bag that opens easily and can sit upright when opened.

It is further an object of the invention to provide a motion sickness bag that is substantially rigid when opened, has a wide mouth, and requires minimal dexterity to use.

It is further an object of the invention to attach a fresh wipe to the bag for handy clean up.

SUMMARY OF THE INVENTION

This invention relates to a liquid receptacle made of a wire frame and material that is substantially impervious to water. The liquid receptacle is capable of being expanded and collapsed for ease of transportation and storage. For ease of use, the receptacle is shaped with a flat bottom allowing it to stand without support, and equipped with a flap surrounding the top opening of the receptacle. For ease of transportation after use, a cord is supplied around the flap for closing the top opening of the liquid receptacle. In one embodiment of the present invention, the liquid receptacle is used for retaining emesis as a result of motion sickness.

The frame of the receptacle is formed of two preferably round wire hoops connected by a wire coil and covered in heavy lined paper or plastic that is preferably biodegradable. The wire structure, when covered with lined paper or plastic, creates a cylinder that is approximately 6 inches high and 6 inches in diameter. This basic design allows the receptacle to be compressed flat for ease of storage and transportation. The receptacle is held in a compressed, and substantially flat state, by fasteners such as, tape, Velcro™ or the like. When the fasteners are released, the receptacle automatically pops open and is ready to be used. When the unit is uncompressed, it forms a cylindrical shape with a flat closed bottom, an open top, and firm sides allowing it to stand upright. In other embodiments of the present invention, the receptacle has a cubical, hexagonal or a rectangular shape.

At least one handle is affixed to the side of the receptacle and can be held during use. A pocket is affixed to the outside of the receptacle and is equipped with a fresh wipe or napkin. A flap, approximately two inches wide, is affixed around the top opening of the receptacle allowing the bag to be closed (or tie-wrapped like a sack) after use. In one embodiment of the present invention, a cord is woven through the flap. This cord enables the user to toggle the flap from a folded position to an upright position to allow the user to close the top opening of the receptacle by tie-wrapping the flap with the cord. In another embodiment, the open end of the receptacle is closed by folding the flap on itself, and holding it in that state using a flat metal wire attached along half of the circumference of the edge of the open end of the flap. This closure system resembles that of a traditional coffee bag.

DETAILED DESCRIPTION

Figure 1:
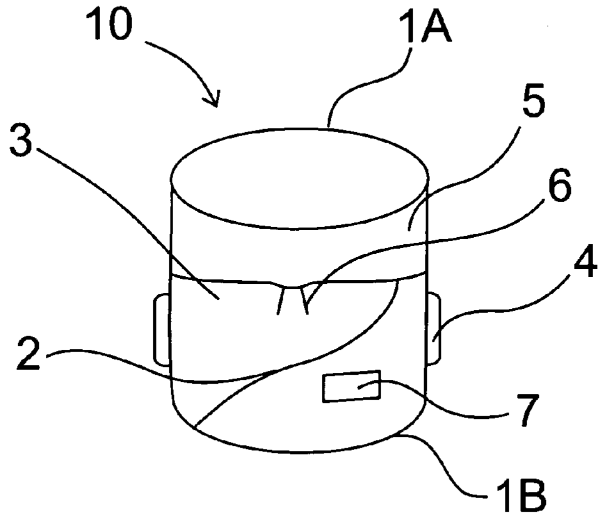
FIG. 1 is a general view of the collapsible liquid receptacle in accordance with the present invention in an uncollapsed state.

FIG. 1 shows the receptacle 10 of the present invention in an uncollapsed open state. As shown in FIG. 1, the receptacle 10 is comprised of material 3 surrounded by a wire frame, which is constructed from a top wire ring 1A, a bottom wire ring 1B, and a wire coil or spring 2. In this embodiment, the wire frame is on the outside on material 3, it is therefore preferred that wire rings 1A and 1B be sewed, glued or affixed in any suitable manner to material 3.

Material 3 is preferably made of a disposable and biodegradable paper or plastic that is substantially impervious to liquid. As appreciated by those skilled in the art, material 3 may be treated with wax or the like to become either water resistant or water proof.

Handles 4 are affixed to the receptacle and used to hold it or carry it. A pouch or pocket 7 is positioned on the outside of the receptacle for holding a fresh wipe. A flap 5 is formed or attached to the top of the receptacle. The flap 5 is preferably about two inches wide. A cord 6 is provided for closing the flap 5. In one embodiment of the present invention, the cord 6 is woven through the flap 5. In another embodiment, the edge of the open end of the flap 5 is folded on itself and held in that state using a flat metal wire attached along half of the circumference of the edge of the open end of the flap 5.

Figure 2:
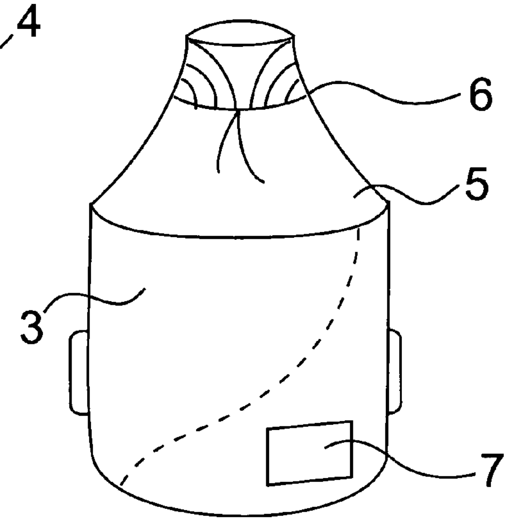
FIG. 2 is a general view of the collapsible liquid receptacle in a closed state and ready for disposal.

FIG. 2 shows the receptacle in an uncollapsed closed state. In this state, the flap 5 is toggled and tightened shut using cord 6. In the embodiment shown in FIG. 2, the frame is contained inside of material 3. Therefore, in this embodiment, it is only necessary to attach the top wire ring 1A to the material, because wire ring 1B pushes against the bottom of material 3 from the inside.

Figure 3:
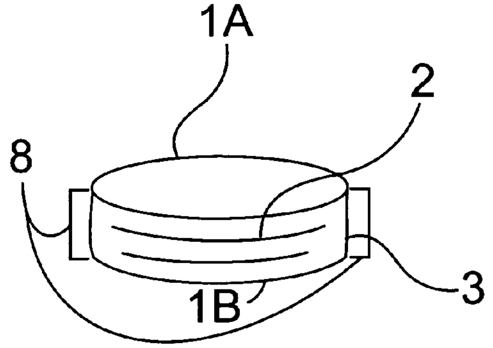
FIG. 3 is a general view of the collapsible liquid receptacle in accordance with the present invention in a collapsed state.

FIG. 3 shows the receptacle in a collapsed state. Wire coil 2 collapses under pressure taking a substantially flat shape for ease of storage and transportation. When collapsed, wire coil 2 stores spring potential energy, and is held in this collapsed state using fasteners 8, which are made of Velcro™, tape or the like. Once the fasteners are unfastened, the stored spring potential energy of coil 2 is released, returning the receptacle to an uncollapsed open, and ready for use state.

In one embodiment of the present invention, fasteners 8 are made of two straps that are long enough to wrap around the receptacle in a collapsed state, and are equipped with Velcro™, tape or the like at their ends. In a collapsed state of the receptacle, the straps are used to fasten the receptacle, while in an uncollapsed state of the receptacle, the straps can be used to carry the receptacle.

Figure 4:
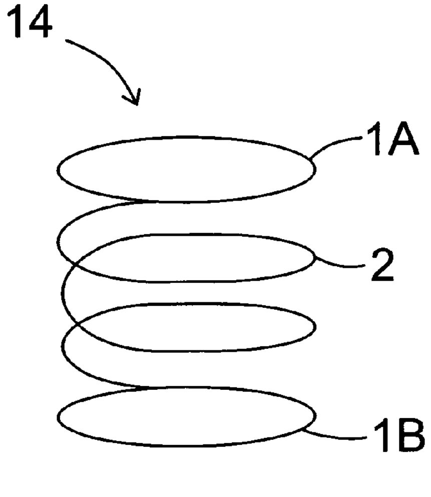
FIG. 4 is a general view of the frame of the collapsible liquid receptacle in accordance with the present invention.

FIG. 4 shows wire frame 14 of the receptacle. Wire frame 14 is made of, for example, aluminum, steel, different alloys, plastic, carbon fiber or the like. Depending on the spring constant of the material and the number of coils used, wire frame 14 may be more or less rigid. Wire frame 14 is formed of top wire ring 1A, coil 2 and bottom wire ring 1B. In an embodiment of the present invention, top wire ring 1A, coil 2 and bottom wire ring 1B are fastened together. In a specific embodiment of the present invention, top wire ring 1A, coil 2 and bottom wire ring 1B are welded together. In yet another embodiment of the present invention, top wire ring 1A, coil 2 and bottom wire ring 1B are formed of a single unitary wire.

In one embodiment of the present invention, coil 2 makes three revolutions going from the bottom wire ring 1B to the top wire ring 1A. A higher number of revolutions gives the structure more rigidity, while a lower number of revolutions gives the structure more flexibility.

In one embodiment of the present invention, wire frame 14 is sewed, glued or affixed in any suitable manner on the inside or the outside of material 3. In another embodiment, wire frame 14 is sandwiched in between two layers of material 3.

Figure 5A:
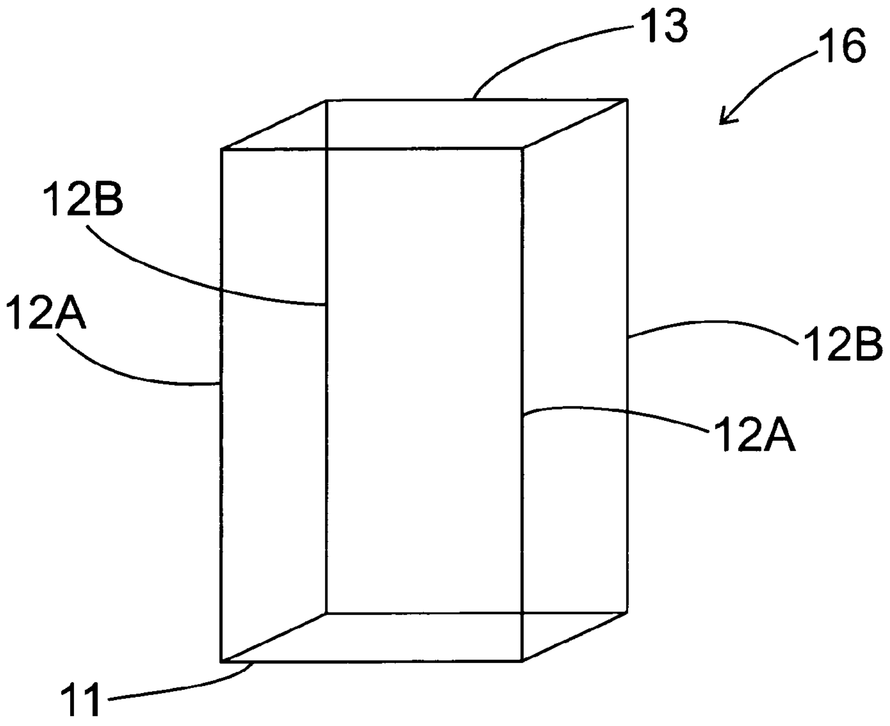
FIG. 5A is a general view of an uncollapsed rectangular frame of the collapsible liquid receptacle.
Figure 5B:
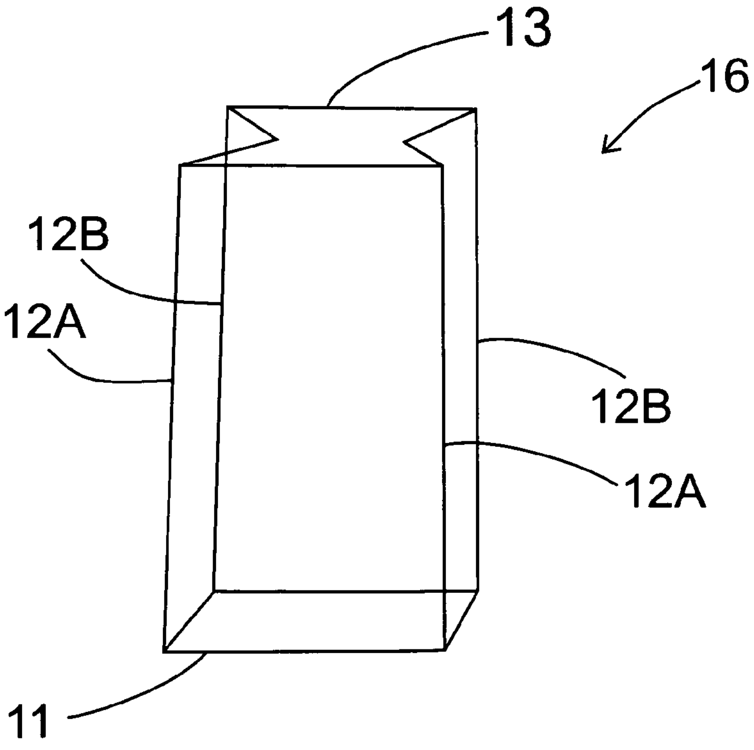
FIG. 5B is a general view of a partially collapsed rectangular frame of the collapsible liquid receptacle.

In the above preferred embodiment of the present invention, the collapsible wire frame 14 has a cylindrical shape. In an alternative embodiment of the present invention, the collapsible wire frame has a cubical shape. In yet another embodiment of the present invention, as shown in FIG. 5A, the collapsible wire frame 16 has a rectangular shape formed of four support legs 12A and 12B respectively attached on one end to the four corners of a lower support frame 11. The other ends of the four support legs 12A and 12B are respectively attached to the four corners of an upper support frame 13. As can be appreciated by a person skilled in the art, this embodiment is adapted to fit within a conventional rectangular motion sickness bag. In fact, conventional motion sickness bags can be retrofitted to incorporate frame 16 as depicted in FIGS. 5A, 5B and 5C.

FIG. 5A demonstrates frame 16 in an uncompressed state forming a rectangular parallelepiped. FIG. 5B demonstrates frame 16 in a partially compressed state, which corresponds to the folding of the side panels of a conventional motion sickness bag. FIG. 5C demonstrates frame 16 in a more fully compressed state, which corresponds to the folding of the bottom panel of the conventional motion sickness bag.

Figure 5C:
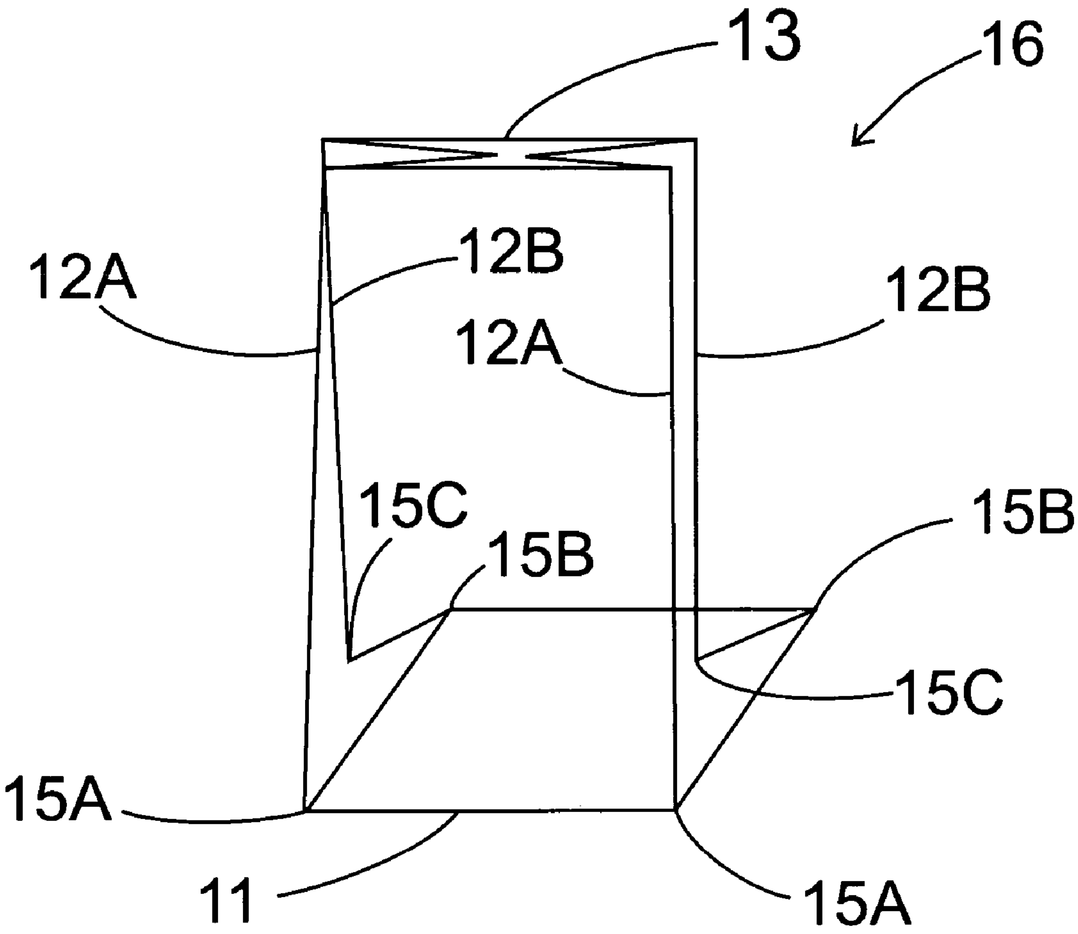
FIG. 5C is a general view of a substantially collapsed rectangular frame of the collapsible liquid receptacle.

FIG. 5C also demonstrates how the support legs 12A and 12B are respectively connected to corners 15A and 15B of the rectangular lower support frame 11. When frame 16 is compressed, legs 12A fold over the lower support frame 11 bending at corners 15A. Legs 12B also fold over the lower support frame 11, bending at corners 15B and bending as well at points 15C on legs 12B. The bends at points 15C are a distance up legs 12B approximately one half the width of lower support frame 11.

The bending of legs 12A and 12B stores spring potential energy in frame 16, which, as discussed above, is held in a compressed state by at least one fastener. When the fastener is removed, the spring potential energy is released causing legs 12A and 12B to spring frame 16 from a compressed state to an uncompressed state.

As appreciated by those skilled in the art, frame 16 in FIGS. 5A, 5B and 5C is made of a material with memory, enabling frame 16 to be compressed to a substantially flat state and held in that position with a fastener. The memory of frame 16 acts as a spring loaded force in the compressed state. When the frame is released, the stored memory returns frame 16 to an uncompressed state. As described above, frame 16 in FIGS. 5A, 5B and 5C can fit either inside or outside of a conventional motion sickness bag. Preferably, however, frame 16 fits on the inside of a conventional sickness bag since this embodiment does not require attaching frame 16 to the motion sickness bag.

Under one manufacturing method of the present invention, a flexible but firm wire is twisted in a shape of a spring to create a spring-loaded collapsible frame. This wire can also be used to form a collapsible frame in another shape, such as, a cube, a rectangle or a hexagon. After forming the frame, a disposable and biodegradable material is affixed to the outside or the inside of the frame. The material may be treated to enhance its ability to retain liquid.

Under another manufacturing method of the present invention, the frame and the material are manufactured separately and attached to each other at a later stage of the manufacturing process. Under yet another manufacturing method of the present invention, the frame and the material are manufactured simultaneously to create the collapsible receptacle.

What is claimed is:

1. A disposable collapsible receptacle for liquids, the receptacle comprising:
   - a wire frame having a collapsed state, wherein the wire frame stores potential energy, and an uncollapsed state, wherein the wire frame releases the stored potential energy; and
   - a biodegradable material attached to the wire frame and capable of retaining liquid.

2. The receptacle according to claim 1, wherein the wire frame is cylindrical in the uncollapsed state.

3. The receptacle according to claim 1, wherein the biodegradable material is water proof.

4. The receptacle according to claim 1, wherein the biodegradable material is water resistant.

5. The receptacle according to claim 1, wherein the receptacle has an open top, the receptacle further comprising a flap of the material for enclosing the open top.

6. The receptacle according to claim 5, further comprising a cord for closing the flap.

7. The receptacle according to claim 1, further comprising at least one external pouch attached to the biodegradable material.

8. The receptacle according to claim 1, further comprising at least one handle attached to the biodegradable material.

9. The receptacle according to claim 1, wherein the wire frame is made of plastic.

10. The receptacle according to claim 1, wherein the wire frame is made of metal.

11. The receptacle according to claim 1, further comprising at least one fastener for holding the receptacle in a collapsed state.

12. The receptacle according to claim 1, wherein the wire frame is contained inside the biodegradable material.

13. The receptacle according to claim 1, wherein the wire frame is on the outside of the biodegradable material.

14. The receptacle according to claim 1, wherein the wire frame is sandwiched between two layers of the biodegradable material.

15. The receptacle according to claim 14, wherein the wire frame is encased in a seam of the biodegradable material.

* * * * *